(12) United States Patent
Cantlon

(10) Patent No.: US 7,191,011 B2
(45) Date of Patent: Mar. 13, 2007

(54) ACCESS PORT INDICATOR FOR IMPLANTABLE MEDICAL DEVICE

(75) Inventor: Kurt Cantlon, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 143 days.

(21) Appl. No.: 10/408,392

(22) Filed: Apr. 7, 2003

(65) Prior Publication Data

US 2004/0199220 A1 Oct. 7, 2004

(51) Int. Cl.
*A61N 1/00* (2006.01)

(52) U.S. Cl. ........................................ 607/60

(58) Field of Classification Search .................. 607/60, 607/92, 122, 90; 604/20, 522; 128/899, 128/908, 903; 600/374, 463, 310, 476
See application file for complete search history.

(56) References Cited

U.S. PATENT DOCUMENTS

| | | | |
|---|---|---|---|
| 3,672,352 A * | 6/1972 | Summers .................... 600/476 |
| 3,699,389 A * | 10/1972 | Holsinger ....................... 361/1 |
| 4,361,153 A * | 11/1982 | Slocum et al. ................. 607/32 |
| 4,706,681 A * | 11/1987 | Breyer et al. ................ 600/374 |
| 5,190,046 A * | 3/1993 | Shturman .................... 600/463 |
| 5,391,199 A * | 2/1995 | Ben-Haim ................... 607/122 |
| 5,445,608 A * | 8/1995 | Chen et al. .................... 604/20 |
| 6,048,359 A * | 4/2000 | Biel ............................. 607/92 |
| 7,107,086 B2 * | 9/2006 | Reihl et al. .................. 600/310 |
| 2002/0055731 A1 * | 5/2002 | Atala et al. .................. 604/522 |

* cited by examiner

*Primary Examiner*—George Manuel
(74) *Attorney, Agent, or Firm*—Peter R. Lando; Christopher S. L. Crawford

(57) ABSTRACT

The invention is directed to an implantable pump. The implantable pump has a port with light emitters indicating the location of the port. The port can be useful in providing bolus injections or the refilling of reservoirs. The light emitters can be arranged in various forms about the port including linear, triangular, square, or circular, among others. If more than one port is located on a device, these ports can be differentiated by differing colors and arrangements of emitters. In addition, various circuitries can be used to activate the emitters. These circuitries can include a coil and capacitor arrangement that provide a separate power source from that of the pump.

5 Claims, 4 Drawing Sheets

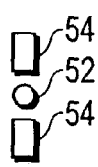
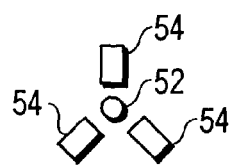
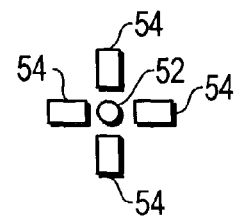
FIG. 3A    FIG. 3B    FIG. 3C
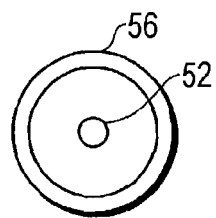
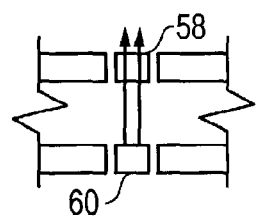
FIG. 3D    FIG. 3E
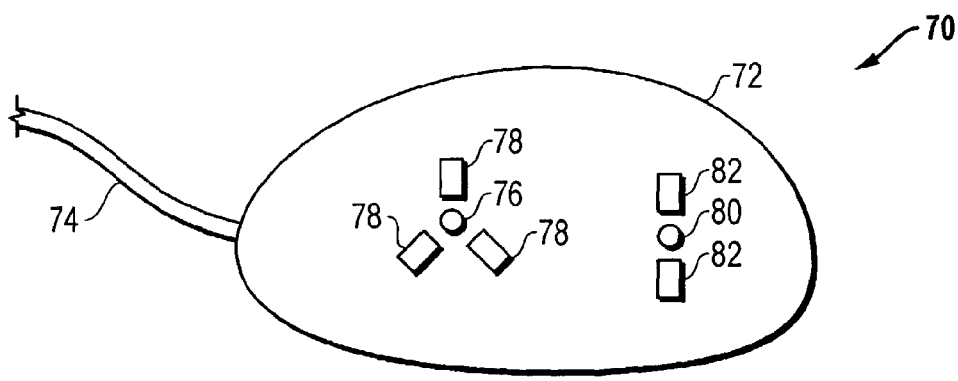
FIG. 4

ACCESS PORT INDICATOR FOR IMPLANTABLE MEDICAL DEVICE

BACKGROUND OF THE INVENTION

Medical devices such as drug infusion pumps are used to treat various ailments and conditions through the delivery of pain medication, anti-spasmatic agents, chemotherapeutic agents, and other pharmaceutical agents. In treating these ailments, the drug infusion pumps can periodically require refilling through a fill access port. In addition, access ports can be provided for bolus injections.

Typically, these devices are placed in fatty tissue under the skin. Access to the ports often is obtained by piercing the skin with a needle or syringe and guiding the syringe through the access port. However, many problems arise in locating the access port and accurately inserting the needle.

If the needle is inserted in the skin at a location relatively far from the access port, the patient can experience additional pain and tissue damage. This tissue damage can be caused by attempting to stretch the tissue and skin to move the needle into position. Alternately, a patient can be stuck in more than one location in an attempt to find the proper location for accessing the port. This repeated sticking and/or jogging of the needle ultimately causes pain, discomfort and tissue damage to the patient.

In addition, attempts to stick the syringe or needle into the access port can cause damage to the needle tip. This damage can scar or core the access port when the needle is inserted or withdrawn, causing a channel or tunnel to be created in the access port. The channel or tunnel can ultimately lead to leaking of pharmaceutical solutions.

As such, typical port access systems suffer from deficiencies in indicating a location of the port and allowing easy and accurate access to the port. Many other problems and disadvantages of the prior art will become apparent to one skilled in the art after comparing such prior art with the present invention as described herein.

SUMMARY OF THE INVENTION

Aspects of the invention are found in an implantable medical device. The implantable medical device such as an implantable drug pump has a port for injecting fluid and a set of energy emitters indicating the location of the port. The device can also have a circuitry coupled to the one or more energy emitters. The energy emitters can be light emitting diodes, edge emitting diodes, or VCSELs, sonic emitters, among emitters. The implantable device can also have a second port and a second set of energy emitters associated with the second port. The second set of energy emitters can emit energy different from that of the first set of the electromagnetic energy emitters. For example, the two sets can display differing colors. The sets of energy emitters can be arranged around the ports in various shapes such as triangles, squares, circles, among others. The ports can be used for bolus injections or refill of reservoirs.

The circuitry connected to the energy emitters can be separate from that of the device and can include a coil. The coil can produce a current in response to an electromagnetic or other energy field. The current causes the emitters to illuminate. The circuit can further have a capacitor, which acts as a charge storage. Alternately, the circuit can have a sensor and switch configuration that turns the emitters on and off.

Additional aspects of the invention are found in a system for transferring fluid to an implantable device. The system has a syringe, an activation device, and an implantable device. The implantable device has a port and a set of energy emitters indicating the location of the port. The implantable device can also have a second port and a second set of energy emitters indicating the location of the second port. The first and second sets of energy emitters can emit energy of differing wavelengths or colors. The sets of energy emitters can be arranged about their associated port in various configurations including triangles, squares and circles. The system can be used for bolus injections or in refilling a reservoir.

Further aspects of the invention are found in a method for indicating a port location. The method includes receiving a signal, and activating energy emitters in response to the signal wherein the energy emitters indicate the location of a port. The method can further include deactivating the emitters to conserve electricity. The step of deactivating can be accomplished by discharging of a capacitor or the opening of a switch, among others. The steps of receiving the signal can include inducing a current in a coil. The method can further include a step of injecting fluid into the port. This injection can take the form of a bolus injection or act to refill a reservoir.

As such, an implantable pump, system for transferring fluid to an implantable device, and method for indicating location of a port are described. Other aspects, advantages and novel features of the present invention will become apparent from the detailed description of the invention when considered in conjunction with the accompanying drawings.

BRIEF DESCRIPTION OF THE DRAWINGS

For a more complete understanding of the present invention and advantages thereof, reference is now made to the following description taken in conjunction with the accompanying drawings in which like reference numbers indicate like features and wherein:

FIGS. 3A, 3B, 3C, 3D and 3E are schematic diagrams depicting exemplary arrangements of emitters, according to the invention;

FIG. 4 is a schematic diagram depicting an exemplary device, according to the invention;

DETAILED DESCRIPTION OF THE INVENTION

Implantable medical devices such as drug infusion pumps are used in various applications to treat various conditions including pain, muscular disorders, and cancer, among others. Periodically, the pumps require refilling. In addition, some pumps permit bolus injections to be administered through an access port. However, problems often arise in locating the ports of medical devices and delivery of materials such as accurately sticking a syringe into the ports.

Figure 1:
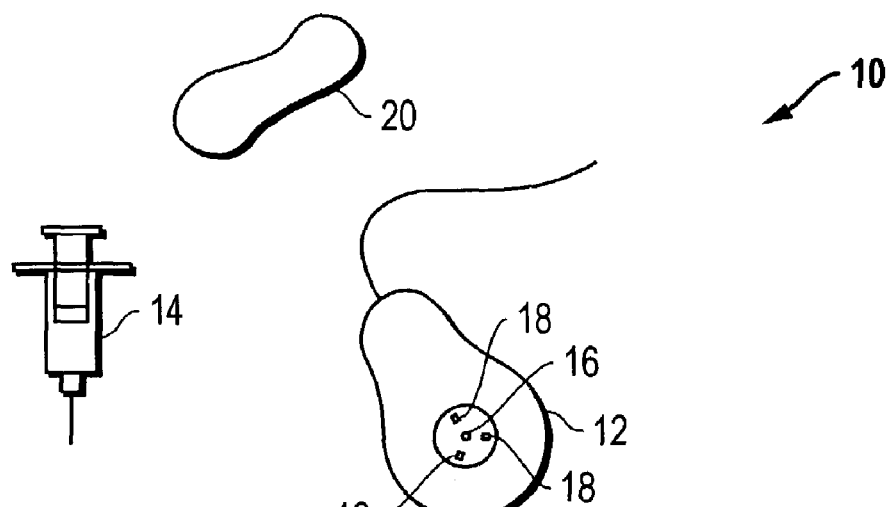
FIGS. 1 and 2 are schematic diagrams depicting exemplary embodiments of an implantable medical device system, according to the invention.

The present invention is directed to a system and method for indicating the location of a port on an implantable medical device, such as a drug infusion pump. FIG. 1 depicts an exemplary system 10 including an implantable pump 12, a syringe 14 and an activation device 20. The implantable pump 12 can have a port 16. The port 16 can permit bolus injections or be useful in refilling a reservoir.

Arranged in proximity to the port can be one or more emitters 18. Emitters 18 can, for example, emit a visible wavelength of light, indicating the location of the port 16. Alternately, the emitters 18 can emit various wavelengths of electromagnetic, sonic or other energy, permitting an external device to locate the port. The emitters may take various forms including bulbs, LEDs, VCSELs, EELs, and fiber optic arrangements, among others. However, various emitters and emitter arrangements can be envisioned.

The implantable pump 12 can also include circuitry that responds to an activation device 20. The circuitry can illuminate the emitters 18 for a period of time in response to a signal or the presence of the activation device 20. In an alternate embodiment, a manipulation mechanism can be include within the pump to activate and/or deactivate the emitters. The circuitry can be separate from or combined with other circuitries within the pump, but various other embodiments can be envisioned.

Figure 2:
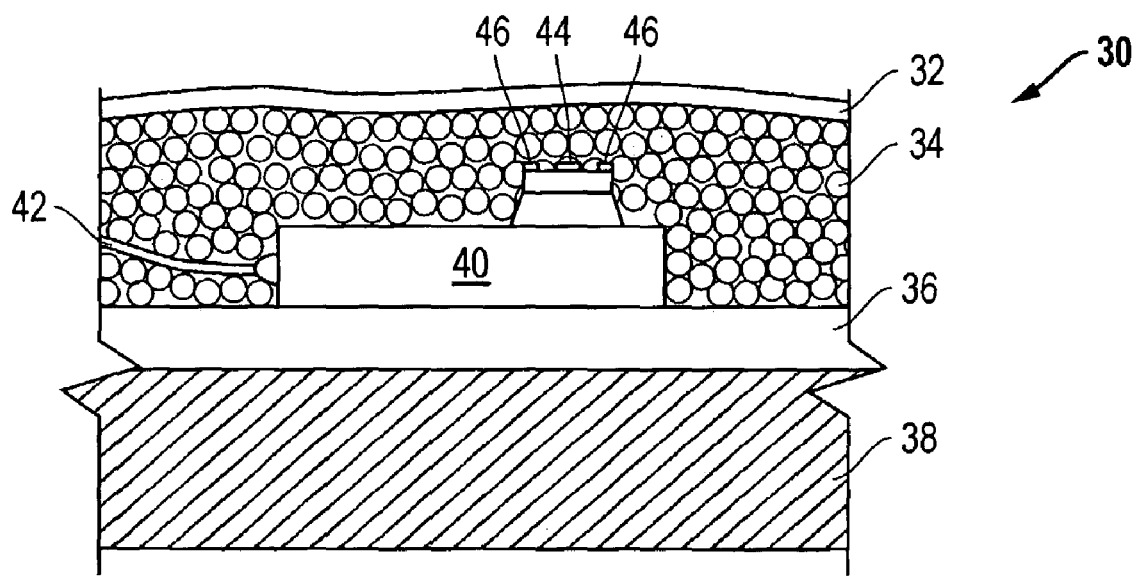

FIG. 2 depicts a placement of the implantable pump 40 in a patient. The placement 30 is shown as a pump 40 located in a fatty tissue 34 below the skin 32 and above the fascia 36 and muscular structure 38. The pump 40 can be placed in the abdominal region, on the side of the patient, or near the lower back, among others locations. From the pump 40, a catheter 42 can carry a treatment solution to a treatment location.

Periodically, the pump 40 requires refilling through a port 44. Emitters 46 can project light, electromagnetic or other energy through the skin indicating the location of the port 44. The port 44 can also be used for injecting a bolus dose.

In the exemplary configurations of FIGS. 1 and 2, the emitters indicate the location of a port, enabling a user to more accurately insert a syringe through the skin 32 and into the port 44. In this manner, damage to the port and syringe can be limited and pain and discomfort in the patient can be reduced.

The emitters can be arranged in various numbers and shapes to indicate the locations of the ports. FIGS. 3A, 3B, 3C, 3D and 3E indicate various arrangements of emitters for indicating a location of a port. For example, FIG. 3A indicates two emitters 54 on opposite sides of the port 52. FIG. 3B depicts a triangular arrangement of three emitters around the port and FIG. 3C depicts a cross or square arrangement of four emitters 54 surrounding a port 52. In an alternate embodiment shown in FIG. 3D, emitters or a single emitter 56 can be arranged around a port 52 in circular arrangement. FIG. 3E shows a further embodiment in which an emitter 60 shines light through a port 58. Various other arrangements can also be envisioned.

FIG. 4 depicts a further embodiment of the system 70. In this embodiment 70, a pump 72 directs a treatment solution through catheter 74. The pump can have two ports 76 and 80. These ports can serve differing functions. For example, one port 76 can act as a bolus injection port while the other port 80 can act as a refill port. However, various functionalities of various ports can be envisaged.

Each port 76 and 80 can have a differing arrangement of emitters. For example, port 76 has a triangular arrangement of three emitters 78, while port 80 has a linear arrangement of two emitters 82. Further, the emitters can emit differing energy. For example, the emitters 78 can emit a different color light than emitters 82.

Implantable pumps often have a limited power supply. Sometimes this is mitigated with the use of transcutaneous energy transfer. Energy can be transferred with the use of an electromagnetic field to a coil in the pump. The electromagnetic field can induce a current or voltage within the coil that recharges batteries or provides power to the pump. The light emitters can draw from the same power source or can operate on a second circuitry to avoid draining power from that source used for providing pump functionality.

Figure 5:
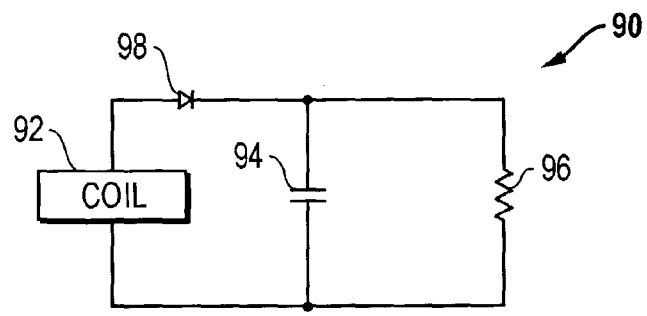
FIGS. 5, 6 and 7 are schematic diagrams depicting exemplary circuits for use in the system as seen in FIGS. 1 and 2.

FIG. 5 depicts an exemplary circuitry for operating the emitters. The circuitry 90 includes a coil 92, a capacitor 94 and one or more emitters 96. An electromagnetic energy field can be induced about the coil 92 from an external source causing charge to flow. This charge can simultaneously build on capacitor 94 and illuminate the emitters 96. Once the field is removed from the coil 92, the capacitor 94 can continue to discharge maintaining, for some period of time, illumination in the emitters 96. Alternately, a diode can be placed 98 in the circuitry to prevent backflow of current through the coil 92. In this manner, the emitters 96 can be illuminated on demand for a period of time during which an injection can be made. Subsequently, the capacitor will discharge, allowing the emitters to dim. The separate circuitry prevents taxing of the power source used to pump fluid to the treatment location.

Figure 6:
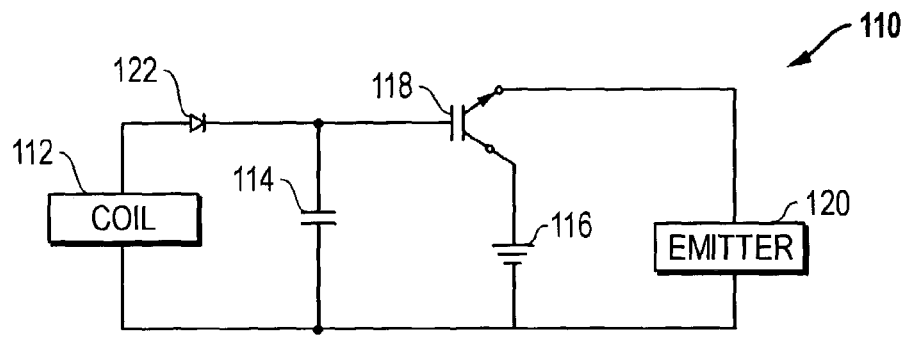

FIG. 6 shows an alternate circuit 110. The circuit includes a coil 112, a capacitor 114, a switch 118, a power source 116, and an emitter 120. The power source 116 can be associated with that of the pump or a separate power source for use with the emitter circuitry. An electromagnetic field induced about the coil 112 can cause a charge to flow. This charge can build on capacitor 114 and initiate the flow of current through a switch 118. For example, the switch 118 can be a transistor. Power from the power source 116 can then flow in a circuit through the emitters 120 causing them to illuminate and indicate the location of a port. Once the electromagnetic field is removed from the coil 112, the capacitor 114 discharges over time. This discharge maintains the position of the transistor 118, allowing for the emitter 120 to continue illuminating the location of the port for a period of time after the electromagnetic field is removed from the coil. A diode 122 prevents electricity from reversing through the coil 112. In this manner, the emitters can be illuminated for a period of time without draining a significant amount of energy from the power source 116.

Figure 7:
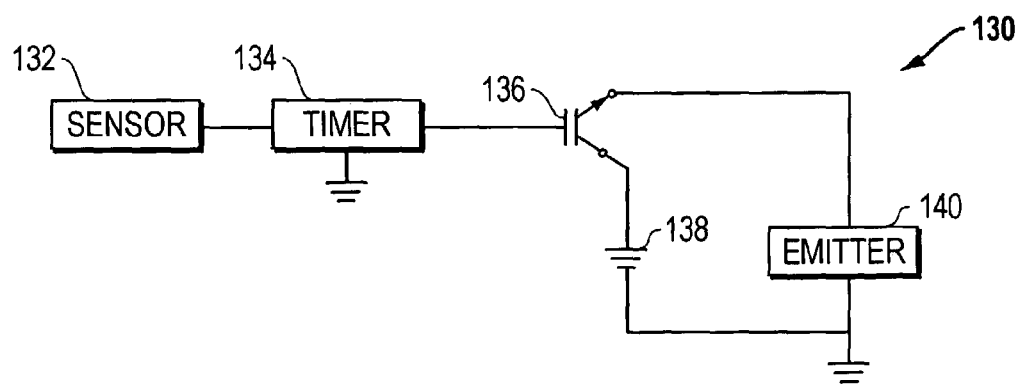

FIG. 7 depicts a further circuitry 130 for causing a timed illumination of the emitters. A sensor 132 can detect the presence of an activation device. The sensor can activate a timer 134, which closes a switch 136. The switch 136 can for example be a transistor. The closing of the switch 136 can direct power from a power source 138 through emitters 140. Upon expiration of a time, the timer 134 can open the switch 136, stopping the flow of electricity through the emitters 140. Alternately, the switch may be opened in response to a signal from the sensor 132.

The sensor 132 can take various forms including a magnetic sensor or a coil, among others. Further, the timer 134 can take various forms including a processor or a timing circuitry, among others. The power source 138 can be a power source of the pump or a separate power source, among others. However, various circuitries can be envisaged to activate or deactivate a emitting source for indicating the location of a port.

Figure 8:
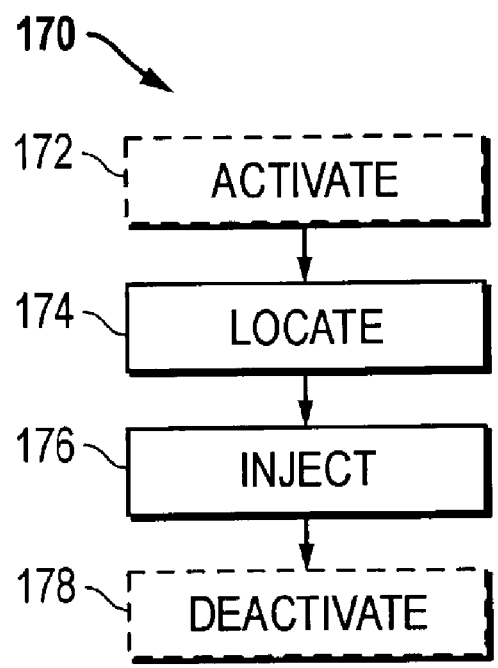
FIGS. 8 and 9 are block flow diagrams depicting exemplary methods for use by the system as seen in FIGS. 1 and 2.

FIG. 8 depicts an exemplary method for using the indicator system on an implantable pump. The method 170 begins with the activation of the light sources as seen in a block 172. This activation can be the inducing of current in a coil, alerting a sensor, manipulating a activator, or other method. The emitters can then illuminate, indicating the location of a port. As seen in a block 174, the port can then be located and a syringe inserted. The fluid can then be injected as seen in block 176. This injection can function as a bolus injection or act to refill a reservoir. The emitters can then be deactivated as seen in block 178. This deactivation can take the form of a discharge of a capacitor or the additional activation of a sensor.

Figure 9:
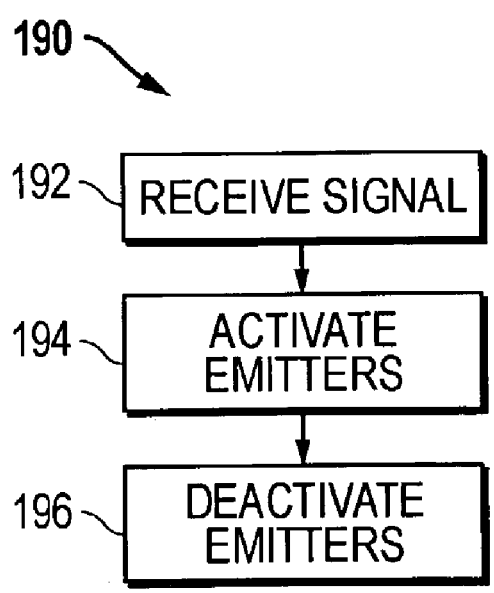

The pump can act as seen in FIG. 9. The method 190 can begin with the receiving of a signal as seen in block 192. The signal can take the form of an electromagnetic or other energy field induced about a coil. For example, the signal can take the form of a magnet over a sensor or a mechanical manipulation. The implantable pump can then activate the emitters as seen in block 194. This activation can result in the illumination of the emitters to indicate the location of a port. After a period of time, the emitters can be deactivated as seen in block 196. This deactivation can take the form of the discharging of a capacitor, additional signaling, or mechanical manipulation of the device, among others.

As such, an implantable pump, system for injecting fluid, and method for indicating the location of a port, are described. In view of the above detailed description of the present invention and associated drawings, other modifications and variations will now become apparent to those skilled in the art. It should also be apparent that such other modifications and variations may be effected without departing from the spirit and scope of the present invention as set forth in the claims which follow.

What is claimed is:

1. An implantable medical device adapted for placement under the skin of a subject, comprising:
   a. a reservoir for storing fluid;
   b. a housing defining a port through which fluid access to the reservoir is obtained;
   c. at least one light emitter adapted for emitting light of a predetermined intensity that is directly viewable through the skin of the subject and is positioned in at least partially surrounding relation to said port, whereby said at least one light emitter non-invasively defines the position of said port; and
   d. circuitry for activating said at least one light emitter.

2. A method of obtaining fluid access to an implantable medical device, comprising:

after the implantable medical device is implanted within a patient, activating at least one light emitter of the implantable medical device in a non-invasive manner using a device external to the patient, wherein the at least one emitter is disposed in at least partially surrounding relation to a fluid port of the implantable medical device;

emitting light from the at least one light emitter of the implantable medical device in response to the activating, wherein the emitted light is of a predetermined intensity that is directly viewable through the skin of the subject; and using the emitted light viewable through the skin of the patient to locate the fluid port and inserting a needle through the skin of the patient through the fluid port into a reservoir of the implantable medical device.

3. The method of claim 2 wherein the at least one emitter is a light emitting diode (LED).

4. The method of claim 2 wherein the at least one emitter is a vertical cavity surface emitting laser (VCSEL).

5. The method of claim 2 wherein the implantable medical device comprises multiple fluid ports and multiple emitters position in relation to the multiple fluid ports with each emitter emitting light of a distinct wavelength to distinguish between the multiple fluid ports.

* * * * *